United States Patent [19]
Andress

[11] 4,071,956
[45] Feb. 7, 1978

[54] METHOD AND MEANS FOR REMOVING DENTAL PLAQUE BY ULTRASONIC VIBRATIONS

[76] Inventor: John Barney Andress, 2 Altamira, Borger, Tex. 79007

[21] Appl. No.: 668,680

[22] Filed: Mar. 19, 1976

Related U.S. Application Data

[63] Continuation of Ser. No. 412,571, Nov. 5, 1973, abandoned.

[51] Int. Cl.² .............................................. A61H 9/00
[52] U.S. Cl. ....................................................... 32/58

[58] Field of Search ........................... 128/62 A; 32/58

[56] References Cited
U.S. PATENT DOCUMENTS

| | | | |
|---|---|---|---|
| 3,401,690 | 9/1968 | Martin | 128/62 A |
| 3,527,218 | 9/1970 | Westline | 128/62 A |
| 3,847,662 | 11/1974 | Massa | 128/62 A |

*Primary Examiner*—Robert Peshock

[57] ABSTRACT

The oral cavity containing a fluid may be employed as a resonance chamber for ultrasonic frequencies applied to the fluid to remove dental plaque.

1 Claim, 3 Drawing Figures

METHOD AND MEANS FOR REMOVING DENTAL PLAQUE BY ULTRASONIC VIBRATIONS

This is a continuation, of application Ser. No. 412,571, filed Nov. 5, 1973 and non abandoned.

BACKGROUND OF THE INVENTION

In general, the present invention relates to a method and means for effecting the removal of food debris and dental plaque from and from between the teeth thus exerting a cleaning action thereon.

More specifically, the present invention relates to a method of producing such cleaning action by employing the oral cavity containing fluid as a resonance chamber for ultrasonic vibrations applied to said fluid and to the means for implementing the same.

The incidence of dental caries and associated periodonal disease is believed, based on substantial evidence, to be connected with the presence and failure to remove food, oral, and carbohydrate debris, materia alba, pellicle, and microbial, dental plaque from and from between the teeth. The conventional manner of removing such debris and plaque is by use of a toothbrush, often aided by a dentifrice and dental floss. The lack of complete success in the education of patients in the need and use of such oral hygiene measures is well known. In addition to the problems of motivation to the daily task and implanting of such a regimen, the topography of the teeth and of the tooth-gingival interfaces, the alignment of the teeth, and the manual dexterity of the patient pose further problems in effecting a satisfactory state of prophylactic oral hygiene.

Power driven toothbrushes have been developed in response to the need to decrease the need for manual dexterity. While these devices have achieved wide acceptance, it is evident that they have not completely solved the problem and that flossing of and between the teeth is still required.

A recent preliminary summary report in *The Journal of the American Dental Association,* September, 1973, vol. 87, no. 3, p. 600–603, by Dr. Henry M. Goldmean indicated the effectiveness of an "ultrasonic-powered toothbrush." Such a toothbrush, however, continues to require the brushing of the individual teeth and thus may face some of the limitations of the prior state of the art.

SUMMARY OF THE INVENTION

Accordingly, it is an object of the present invention to provide a new, highly effective method, and means for implementing the same, which overcomes the deficiences of the prior art as described above.

It is a further object of the present invention to provide a new, highly effective method for the removal of food, oral, and carbohydrate debris, materia alba, pellicle and microbial, dental plaque from and from between the teeth.

Another object of the present invention is to provide a quick, highly efficient method, and means for implementing the same, which requires minimal manual dexterity and is minimally affected by the topography and alignment of the teeth and of the tooth-gingival interfaces.

Other objects and a fuller understanding of the present invention may be had by referring to the following description and claims taken in conjunction with the accompanying drawings.

The present invention overcomes the deficiencies of the prior art and achieves its objectives by utilizing the oral cavity substantially filled with fluid as a resonance chamber for ultrasonic frequencies applied to the fluid to remove dental plaque and the like.

BRIEF DESCRIPTION OF THE DRAWINGS

In order to facilitate the understanding of the present invention, reference will now be made to the appended drawings illustrative of preferred embodiments of the present invention. The drawings are not to be construed as limiting the invention but are exemplary only. In the drawings.

DESCRIPTION OF THE PREFERRED EMBODIMENTS

A sound wave is a succession of periodic variations of pressure in a medium in which molecules are momentarily displaced from their equilibrium positions and thence restored by forces due to the elasticity of the medium, resulting in the propagation of the disturbance wave in the form of an oscillation of the molecules about their mean positions.

When the frequency of vibration is in a range of 20 to 15,000 Hz (cycles per second) the sound wave is audible to the human ear.

Above 15,000 Hz such waves are termed ultrasonic. The range of ultrasonic vibrations producible with the current state of the art is from 15,000 Hz up to frequencies on the order of 20 billion Hz (cycles per second) or 20 kilomegacycles.

For a given intensity, the displacement amplitude is inversely proportional to the frequency. A striking feature of ultrasonic vibrations is the very large magnitude of particle acceleration as compared with particle displacement which may typically be over a million times the acceleration due to gravity.

A ultrasonic wave of a frequency or $10^6$ Hz in water undergoes a first order sinusoidal change in pressure from a pressure on the order of magnitude of + 60 atm to − 60 atm and back to + 60 atm a million times a second, taking the ambient pressure as the zero point.

The above described action provides for and causes vaporous and gaseous cavitation due to the formation of bubbles by gases coming out of solution under the cyclical pressure changes followed almost immediately by their subsequent collapse and implosion, producing "cold boiling."

Ultrasonic vibrations may be produced by mechanical flow or piston devices or by an electronic frequency generator such as an oscillator and high output amplifier coupled to a magnetostrictive transducer or an inverse piezoelectric transducer.

The nature and creation of ultrasonic vibrations as discussed herein is provided for completeness of the description of the combination of the present invention and does not per se constitute the invention. A further description of ultrasonics may be had by reference to B. Brown et al, *High Intensity Ultrasonics: Industrial Applications,* (1965); O. I. Babikov, *Ultrasonics and Its Indus-* trial Applications, (1960); J. Blitz, *Fundamentals of Ultrasonics,* (1968); B. Carlin, *Ultrasonics,* (1960); A. E. Crawford, *Ultrasonic Engineering,* (1955); I. E. El'piner, *Ultrasound Physical, Chemical, and Biological Effects,* (1964); J. R. Frederick, *Ultrasonic Engineering,* (1965); E. G. Richardson, *Ultrasonic Physics* (1962); E. Ackerman, *Biophysical Science* (1962); K. E. Herzfeld et al, *Absorption and Dispersion of Ultrasonic Waves,* (1959); and E. Kelly, ed., *Ultrasonic Energy: Biological Investigations and Medical Applications,* (1965).

Figure 1:
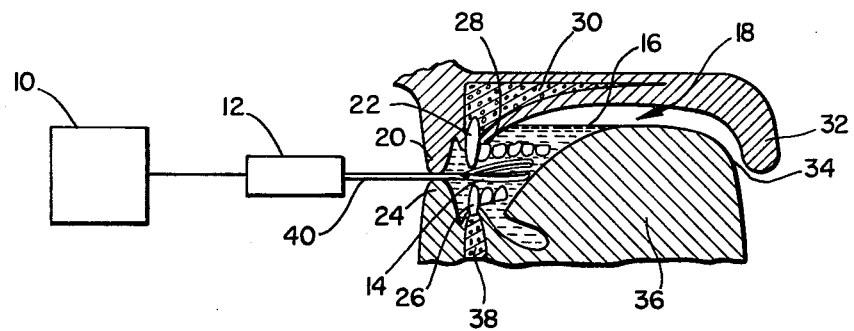
FIG. 1 is a partial cross-sectional side-elevational schematic representation of the present invention.

A preferred embodiment of the present invention is shown in FIG. 1 in which 10 is an electronic frequency generator and 12 is a transducer of the magnetostrictive or inverse piezoelectric type for converting the electronic frequencies from 10 to ultrasonic vibrations.

The ultrasonic vibrations are transmitted to a vibrational element 14 which is placed within a fluid 16 in the oral cavity 18.

For the purposes of the description of the present invention the oral cavity refers not only to the space between the upper lip 20 and upper teeth 22 and the lower lip 24 and lower teeth 26 but also to the cavity bounded by the cheeks (not shown), the teeth ridge 28, the hard palate 30, the soft palate 32, the back of the tongue 34, the tongue 36 and mandible 38. The oral cavity as referred to herein is further defined and enumerated in F. Frohse, *Atlas of Human Anatomy* (1935).

The function of the vibrational element 14 is to transmit the ultrasonic vibrations to the fluid 16 which substantially fills the oral cavity 18, thereby inducing in the fluid ultrasonic vibrations and cavitation to effect the desired cleaning of the teeth and removal of the dental plaque.

Figure 2:
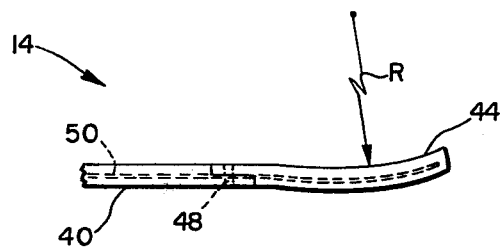
FIG. 2 is a side-elevational representation of the vibrational element of the present invention.
Figure 3:
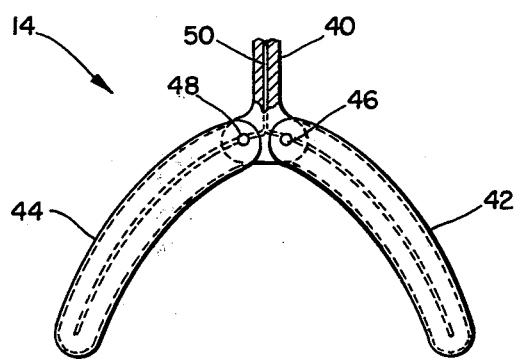
FIG. 3 is a top-plan view of the vibrational element of the present invention.

To this end a preferred embodiment of a typical vibrational element 14 is shown in further detail in FIGS. 2 and 3. A handle 40 which further serves to transmit the ultrasonic vibrations from transducer 12 to the main body of the vibrational element 14 may be pivotally connected by pins, 46, 48 to adjustable arms 42, 44 to provide an adjustably parabolic, catenary configuration which corresponds to the general configuration of the array of human teeth. In this embodiment only two sizes of such vibrational elements 14 are required: one for the average adult mouth, another for the pedo mounth. In addition to the adjustable parabolic, catenary configuration conforming to the array of human teeth, the vibrational element 14 is curved in the vertical plane with a radius of curvature R which is well known in the dental sciences as the Curve of Spee so as to further conform to the configuration of the human teeth.

In an alternative embodiment of the above described vibrational element 14, the vibrational element 14 may be formed as a single unitary structure; however such a structure would necessitate the production of a multiplicity of sizes to enable a reasonable correspondence between the vibrational element 14 and the various arrays of teeth.

The materials of construction of the vibrational element are largely immaterial; however it is desirable that the materials be sufficiently rigid and have a high coeffecient of transmittance of ultrasonic frequencies. The common metals, glass, various ceramic, as well as hard plastics and rubbers are generally suitable.

If it is desired to augment the transmittance of the ultrasonic frequencies in a given selected material, a metallic element 50 may be employed centrally of the members of vibrational element 14.

If gaseous ultrasonic waves are the selected mode of operation, the element 50 may be a tube in which ultrasonic standing waves may be developed.

As further embodiments of the above preferred embodiment, it may be preferred in all cases to cover the vibrational element 14 with a soft plastic or elastomeric material to prevent inadvertent injury to any of the teeth by the ultrasonic vibrations of element 14. Further such protective elements and/or guards (not shown) may also be added in the area in which the lips close on the vibrational element 14.

In addition to such protective coatings, therapeutic coatings of dentifrice materials may be coated on the vibrational element 14 to flake off under the action of the ultrasonic vibrations of the fluid 16.

Yet another embodiment of the present invention comprises forming the vibrational element 14 from a moldable ferroelectric or piezoelectric material such as barium titanate ($BaTiO_3$), barium lead titanate, barium calcium titanate or lead zirconatetitanante. In this embodiment the vibrational element 14 would perform its usual functions as well as serving as and in lieu of the transducer 12.

Vibrational element 14 may also embody additional passages to allow the injection of the fluid 16 into the oral cavity 18 through the element 14, if desired.

The fluid 16 may be water alone or a weak (approx. 10%) sodium chloride solution. In the use of such a weak salt solution the salt particles under the influence of the ultrasonic vibrations will assist in the removal of dental plaque from the teeth.

Other materials may also be added to fluid 16 to aid in the cleaning action or for other therapeutic reasons. For example, such additional materials as may be added include fine silicone particles, silica particles, sodium alumino silicates and other well known cleaning and polishing agents as well as antibacterial, anticaries, and antienzyme agents. Typical examples of such combinations of ingredients are found for example in U.S. Pat. Nos. 3,081,235; 3,450,813; 3,510,553; 3,574,824; 3,622,662; 3,624,198; 3,626,056; 3,634,585; 3,642,979; 3,662,059; 3,662,060; 3,678,155; 3,683,065; 3,692,894; 3,703,578; 3,705,940; and in British Pat. Nos. 868,466; 923,079; 1,186,706; 1,241,877; 1,264,292; 1,304,090; and in Canadian Pat. Nos. 627,822; 914,069 and in *Dentifrices,* T. Jefopoulcs (1970). In any case in addition to the cleaning, polishing, and therapeutic properties provided in any fluid formulation for use in the present invention, the formulation must be nontoxic, nonsensitizing, nonirritating and stable under the conditions of preparation, storage and use including ultrasonic frequency vibrations.

In operation, vibrational element 14 is placed in the oral cavity of the patient (or other user) and the patient takes a drink of the desired fluid 16 in an amount sufficient to substantially fill the oral cavity 18 and holds the fluid in his mouth by holding the tongue back, closing the lips and providing a slight positive, outward pressure such as may cause the cheeks to bulge out. The electronic frequency generator 10 is then turned on and as a result of the action of transducer 12 the vibrational element 14 is caused to vibrate at ultrasonic frequencies within the fluid 16 held in the oral cavity 18.

The ultrasonic vibration and cavitation of fluid 16 produced by element 14 is continued for less than one minute during which period the teeth are effectively cleaned of dental plaque.

The device is then turned off and the fluid 16 expelled from oral cavity 18 and the vibrational element 14 removed from the oral cavity 18.

The above noted sequence of entering and removing the vibrational element 14 and the fluid 16 from the oral cavity 18 may be reversed as a matter of preference by individuals and may be assisted by employment of the above described embodiment providing for injection of the fluid through vibrational element 14.

Thus, in summary, the above described operation utilizes the oral cavity filled with fluid as a resonance cavity for the ultrasonic vibrations and cavitation of said fluid to effect substantial removal of the dental plaque from and from between the teeth.

Although a specific preferred embodiment of the present invention has been described in the detailed description provided above, the description is not intended to limit the invention to the particular forms or embodiments disclosed herein, since they are to be recognized as illustrative rather than restrictive and it will be obvious to those skilled in the art that the invention is not so limited. For example, other shapes and forms of the vibrational element 14 may be employed without departing from the spirit and scope of the present invention. The invention is thus declared to cover all changes and modifications of the specific examples of the present invention herein disclosed for the purposes of illustration, which do not constitute departures from the spirit and scope of the present invention.

What is claimed is:

1. A device for removing dental plaque from and from between teeth by employing the oral cavity substantially filled with sufficient liquid to cover and surround said teeth as a resonance chamber for applied ultrasonic vibrations comprising: means for producing electromagnetic signal oscillations in excess of 15,000 Hz (cycles per second); means for transducing said electromagnetic signal oscillations to an ultrasonic frequency vibration; and means for applying said ultrasonic frequency vibrations to said liquid within said oral cavity to induce thereby ultrasonic frequency vibrations and cavitation within said liquid and within said oral cavity whereby said dental plaque may be removed from and from between said teeth by the said ultrasonic frequency vibrations and cavitation induced within said oral cavity and said liquid by said applied ultrasonic frequency vibrations, wherein the said means for applying said ultrasonic frequency vibrations to said liquid within said oral cavity to induce thereby ultrasonic frequency vibrations and cavitation within said liquid and with said oral cavity comprises vibrating means having a parabolic configuration in the horizontal plan corresponding to the general array of teeth in the oral cavity and a radius of curvature in the vertical plane corresponding to the Curve of Spee, and the said vibrating means is adjustable by virtue of having each of the arms of the parabolic configuration pivotable annd rotatable substantially in the horizontal plane about a point at the vertex of said parabolic configuration.

* * * * *